(12) United States Patent
Rosenbaum et al.

(10) Patent No.: US 12,385,894 B2
(45) Date of Patent: Aug. 12, 2025

(54) SYSTEMS AND METHODS FOR CHARACTERIZING SURFACTANT PROTEIN D (SP-D) OLIGOMERS

(71) Applicant: Airway Therapeutics, Inc., Marietta, GA (US)

(72) Inventors: Jan Susan Rosenbaum, Cincinnati, OH (US); Mark Cornell Manning, Johnstown, CO (US); Ryan R. Manning, Charlotte, MI (US)

(73) Assignee: Airway Therapeutics, Inc., Marietta, GA (US)

( * ) Notice: Subject to any disclaimer, the term of this patent is extended or adjusted under 35 U.S.C. 154(b) by 1057 days.

(21) Appl. No.: 17/041,682

(22) PCT Filed: Mar. 27, 2019

(86) PCT No.: PCT/US2019/024320
§ 371 (c)(1),
(2) Date: Sep. 25, 2020

(87) PCT Pub. No.: WO2019/191254
PCT Pub. Date: Oct. 3, 2019

(65) Prior Publication Data
US 2021/0010988 A1 Jan. 14, 2021

Related U.S. Application Data

(60) Provisional application No. 62/650,138, filed on Mar. 29, 2018.

(51) Int. Cl.
| | | |
|---|---|---|
| *G01N 33/15* | (2006.01) | |
| *C12Q 1/02* | (2006.01) | |
| *G01N 33/50* | (2006.01) | |
| *G01N 33/94* | (2006.01) | |

(52) U.S. Cl.
CPC ............. *G01N 33/15* (2013.01); *C12Q 1/025* (2013.01); *G01N 33/5041* (2013.01); *G01N 33/94* (2013.01); *G01N 2500/10* (2013.01)

(58) Field of Classification Search
None
See application file for complete search history.

(56) References Cited

U.S. PATENT DOCUMENTS

| | | |
|---|---|---|
| 8,865,643 B2 | 10/2014 | Clark et al. |
| 9,370,555 B2 | 6/2016 | Whitsett et al. |
| 2011/0189104 A1 | 8/2011 | Whitsett et al. |
| 2011/0256133 A1 | 10/2011 | Dixit et al. |
| 2013/0316980 A1 | 11/2013 | Tchirikov |
| 2014/0302158 A1 | 10/2014 | Cabrera et al. |
| 2015/0335578 A1 | 11/2015 | Spira et al. |
| 2017/0189527 A1 | 7/2017 | Rinaldi et al. |
| 2019/0071693 A1 | 3/2019 | Rosenbaum et al. |
| 2019/0071694 A1 | 3/2019 | Rosenbaum et al. |
| 2021/0121536 A1 | 4/2021 | Rosenbaum et al. |

FOREIGN PATENT DOCUMENTS

| | | |
|---|---|---|
| EP | 1132402 | 9/2001 |
| JP | 2003-514864 A | 4/2003 |
| JP | 2006-522751 A | 10/2006 |
| JP | 2009-514958 A | 4/2009 |
| JP | 4744533 B2 | 8/2011 |
| RU | 2603093 | 5/2014 |
| RU | 2643762 | 12/2016 |
| WO | WO 2001/080633 | 11/2001 |
| WO | WO 2012/093087 | 7/2012 |
| WO | WO 2017/143024 | 8/2017 |
| WO | WO 2019/191247 | 10/2019 |

OTHER PUBLICATIONS

Yohannes, G., et al. 2011 Journal of Chromatography A 1218: 4104-4116. (Year: 2011).*
Wyatt Technology Corporation Astra V User's Guide 2008: 372 pages. (Year: 2008).*
Crouch, E.C. 1998 Am. J. Respir. Cell Mol. Biol. 19: 177-201. (Year: 1998).*
Hartshorn, K. et al. "Interactions of recombinant human pulmonary surfactant protein D and SP-D multimers with influenza A." Am. J. Physiol, vol. 271 No. 5, pt. 1, 1996, pp. L753-L762.
Kuroki, Y. "Innate immune function of pulmonary collectins." Biochemistry, vol. 81 No. 3, 2009, pp. 182-188.
Kuroki, Y. "Pulmonary Surfactant Proteins: SP-A and SP-D." Clinical Chemistry, vol. 32, 2003, pp. 216-226.
Kuroki, Y. "Collectin (SP-A, SP-D, MBL) and Infection Prevention." Modern Medical Laboratory, vol. 42 No. 5, May 1, 2014, pp. 488-489.
Zherdev V.P et al. "Preclinical study the pharmacokinetics new anxiolytic drug of dipeptide structure GB-115." Pharmacokinetics and Pharmacodynamics, vol. 1, 2015, pp. 52-59. (abstract only).
Kalmatov, R.K. et al. "Pathogenetic Role of Surfactant Protein Sp-D at Diseases Lungs and Airways." Fundamental Research, No. 1, 2015, pp. 1591-1595.
"Respiratory Medicine." A.G. Chuchalin, Ed., 2017, available at https://cpkmed.ru/materials/El_Biblio/AktualDoc/ftiziatrija/4.pdf.
Pozza G.M.-E. et al., Molecular and structural characterization of hybrid poly(ethylene oxide)-polyhedral oligomeric silesquioxanes star-shaped macromolecules, Phys Chem B, 2015, V.119, N. 4, p. 1669-1680. (Abstract only).
Sluchanko N.N. et al., Monomeric 14-3-3ζ Has a Chaperone-Like Activity and Is Stabilized by Phosphorylated HspB6, Biochemistry, 2012, V. 51, N. 31, p. 6127-6138. (Abstract only).
Koeffler P. et al., Human Myeloid Leukemia Cell Lines: A Review, Blood, 1980, V. 56, I. 3, p. 344-350. (Abstract only).

(Continued)

*Primary Examiner* — Marsha Tsay
(74) *Attorney, Agent, or Firm* — Quicker Law, LLC (57) ABSTRACT

Some embodiments of the methods and compositions provided herein include identifying and/or quantifying oligomeric species of surfactant protein-D (SP-D). Some embodiments include performing an asymmetric flow field-flow fractionation with multi-angle laser light scattering (AF4-MALLS) analysis on the SP-D.

11 Claims, 1 Drawing Sheet
Specification includes a Sequence Listing.

(56) References Cited

OTHER PUBLICATIONS

Sorensen, G. "Surfactant Protein D in Respiratory and Non-Respiratory Disesases," Sec. Pulmonary Medicine. (2018) 5: 1-37.
Wong, W. et al., "FungalmelaninstimulatessurfactantproteinD-mediated opsonization of and host immune response to Aspergillus fumigatus spores," J. Biol. Chem. (2018) 293(13): 4901-4912.
Nousheen, L., et. al., "Molecular Docking and Mutational Studies of Human Surfactant Protein-D," World J. Pharm. Res. (2014) 3(7): 1140-1147.
Sim, R. "SP-D," The Complete FactsBook. (2000): 46-50.
Uniprot, Commercially available sequence for recombinant human SP-D. retrieved from https://www.uniprot.org/uniprotkb/P35247/entry#sequences on Oct. 10, 2023.
Watson, A. S. "Recombinant Expression of Functional Trimeric Fragments of Human SP-A and SP-D," University of Southampton, Faculty of Medicine, PhD Thesis (2016).
International Search Report and Written Opinion mailed Jul. 12, 2019 in PCT/US2019/024320 (16 pgs.).
Mehn, D. "FFF-MALS method development and measurements of size and molecular weight", EUNCL, Doc. ID EUNCL-PCC-22, Jan. 30, 2016, 27 pgs.
Arroyo et al. Structural Characterization of Human Pulmonary Surfactant Protein SP-D by Atomic Force Microscopy. Biophysical J. (2017) 112(3):503a Abstract 2478-Pos.
Arroyo et al., Supramolecular Assembly of Human Pulmonary Surfactant Protein SP-D. J Mol Biol. (2018) 430(10):1495-1509.
Awasthi S., Surfactant protein (SP)-A and SP-D as antimicrobial and immunotherapeutic agents. Recent Pat Antiinfect Drug Discov. (2010) 5(2):115-123.
Clark et al., Structural requirements for SP-D function in vitro and in vivo: therapeutic potential of recombinant SP-D. Immunobiology (2002) 205(4-5):619-631.
Clements J.A., Functions of the alveolar lining, Am Rev Respir Dis (1977) 115(6 Pt 2):67-71.
Crouch et al., Molecular structure of pulmonary surfactant protein D (SP-D). J Biol Chem. (1994) 269(25):17311-17319.
Crouch E.C., Surfactant protein-D and pulmonary host defense. Respir Res. (2000) 1(2):93-108.
Crouch et al., Contributions of phenylalanine 335 to ligand recognition by human surfactant protein D: ring interactions with SP-D ligands. J Biol Chem., (2006) 281(26):18008-18014.
Debye P., Molecular-weight determination by light scattering. J Phys Chem., (1947) 51:18-32.
Dodagatta-Marri et al., Purification of surfactant protein D (SP-D) from pooled amniotic fluid and bronchoalveolar lavage. Methods Mol Biol. (2014) 100:273-290.
Griese M., Pulmonary surfactant in health and human lung diseases: State of the art, Eur Respir J (1999) 13:1455-1476.
Haagsman et al., Surfactant collectins and innate immunity. Neonatology (2008) 93:288-294.
Håkansson et al., Collectin structure: a review. Protein Sci. (2000) 9:1607-1617.
Hartshorn et al., Role of viral hemagglutinin glycosylation in anti-influenza activities of recombinant surfactant protein D. Resp Res. (2008) 9(1):65 in 12 pgs.
Ikegami et al., Intratracheal Recombinant Surfactant Protein D Prevents Endotoxin Shock in the Newborn Preterm Lamb. Am J Respir Crit Care Med. (2006) 173(12):1342-1347.
Kingma et al., Correction of pulmonary abnormalities in Sftpd-/- mice requires the collagenous domain of surfactant protein D. J Biol Chem. (2006) 281:24496-24505.
Knudsen et al. A recombinant fragment of human surfactant protein D lacking the short collagen-like stalk fails to correct morphological alterations in lungs of SP-D deficient mice. The Anatomical Record (2009) 292(2):183-189.
Knudsen et al., Surfactant protein D (SP-D) deficiency is attenuated in humanised mice expressing the Met(11)Thr short nucleotide polymorphism of SP-D: implications for surfactant metabolism in the lung. J Anat. (2013) 223(6):581-592.
Korfhagen et al., Surfactant protein-D regulates surfactant phospholipid homeostasis in vivo. J Biol Chem. (1998) 273(43):28438-28443.
Malash et al., Association of TLR polymorphisms with bronchopulmonary dysplasia. Gene (2016) 592(1):23-28.
Ogasawara et al., The role of the amino-terminal domain and the collagenous region in the structure and the function of rat surfactant protein D. J Biol Chem. (1995) 270(32):19052-19058.
Robertson et al., Principles of surfactant replacement, Biochim Biophys Acta (1998) 1408:346-361.
Sato et al., Surfactant Protein-D Inhibits Lung Inflammation Caused by Ventilation in Premature Newborn Lambs. Am J Respir Crit Care Med. (2010) 181(10):1098-1105.
Strong et al., A novel method of purifying lung surfactant proteins A and D from the lunglavage of alveolar proteinosis patients and from pooled amniotic fluid. J Immunol Methods. (1998) 220(1-2):139-149.
Vieira et al., Structure, Genetics and Function of the Pulmonary Associated SurfactantProteins A and D: The Extra-Pulmonary Role of These C Type Lectins.Ann Anat. (2017) 211:184-201.
Wagner et al., Asymmetric flow field-flow fractionation in the field of nanomedicine. Anal Chem (2014) 86(11):5201-5210.
Wert et al., Increased metalloproteinase activity, oxidant production, and emphysema in surfactant protein D gene-inactivated mice. PNAS (2000) 97(11): 5972-5977.
White et al., Multimerization of surfactant protein D, but not its collagen domain, is required for antiviral and opsonic activities related to influenza virus. J Immunol. (2008) 181(11):7936-7943.
Winkler et al., Impact of a Met(11)Thr single nucleotide polymorphism of surfactant protein D on allergic airway inflammation in a murine asthma model. Exp Lung Res. (2014) 40(4):154-163.
Wold et al., PLS-regression: a basic tool of chemometrics. Chemom. Intell. Lab. Syst. (2001) 58: 109-130.
Yamazoe et al., Pulmonary surfactant protein D inhibits lipopolysaccharide (LPS)-inducedinflammatory cell responses by altering LPS binding to its receptors. J Biol Chem. (2008) 283(51):35878-35888.
Zhang et al., Activity of pulmonary surfactant protein-D (SP-D) in vivo is dependent on oligomeric structure. J Biol Chem (2001) 276(22):19214-19219.
Zimm B.H., The scattering of light and the radial distribution function of high polymer solutions. J Chem Physics (1948) 16(12):1093-1099.
Zuo et al., Current perspective in pulmonary surfactant—Inhibition, enhancement and evaluation, Biochim Biophys Acta (2008) 1778:1947-1977.
Bharate et al., Interactions and incompatibilities of pharmaceutical excipients with active pharaceutical ingredients: A comprehensive review. J Excipients and Food Chem. (Nov. 2016) 1(3): 1131 in 24 pages.
Brooke et al., Universal buffers for use in biochemistry and biophysical experiments. AIMS Biophysics. (2015) 2(3): 336-342.
Carpenter et al., Rational design of stable lyophilized protein formulations: Theory and practice, rational design of stable protein formulations. Pharma Biotech. (2002) 109-127.
Muller et al., Spliceosomal peptide P140 for immunotherapy of systemic lupus erythematosus: Results of an early phase II clinical trial. Arth Rheuma. Official J Am College of Rheuma. (Dec. 2008) 58(12): 3873-3883.
Patel et al., Drug-excipient compatibility studies: First step for dosage form development. TPI Inter'l J. (2015) 4(5): 14-20.
Sako et al., Characterization of the ligand binding functionality of the extracellular domain of activin receptor type IIB. J Biol Chem. (Jul. 2010) 285(27): 21037-21048.
Schaefers, M., Reconstructing reconstitution. Packaging Digest (2015) downloaded from https://www.packagingdigest.com/sterilization/reconstructing-reconsitution; 3 pages.
Tang et al., Design of freeze-drying processes for pharmaceuticals: Practical advise. Pharm Res. (2004) 21(2): 191-200.
Tonnis et al., Size and molecular flexibility of sugars determine the storage stability of freeze-dried proteins. Mol Pharm. (2015) 12: 684-694.

(56) References Cited

OTHER PUBLICATIONS

Vuk-Pavlovic et al., Carbohydrate recognition domain of surfactant protein D mediates interactions with Pneumocystic carinii glycoprotein A. Am J Respir Cell Mol Biol. (2001) 24(4): 475-484.

Stahle, L. et al. "Multivariate Data Analysis and Experimental Design in Biomedical Research." Progress in Medicinal Chemistry, vol. 25, 1988, pp. 291-338. (Abstract only).

Manning, R. et al. "Characterization of Oligomer Formation of Surfactant Protein-D (SP-D) Using AF4-MALLS." Current Protein and Peptide Science, vol. 23, 2022, pp. 862-873.

Sano, H. et al. "The lung collectins, SP-A and SP-D, modulate pulmonary innate immunity", Molecular Immunology, vol. 42, 2005, pp. 279-287.

Sarker et al., Lung Surfactant Protein A (SP-A) Interactions with Model Lung Surfactant Lipids and an SP-B Fragment. Biochem. (Jun. 2011), 50(22): 4867-4876.

White et al., Increased antiviral and opsonic activity of a highly multimerized collectin chimera. Biochem Biophys Res Commun. (2001) 286: 206-213.

Some, D. "The Chromatography Detector You Shouldn't Miss", Nov. 20, 2015, at https://www.wyatt.com/blogs/the-chromatography-detector-you-shouldn-t-miss.html.

Rynkiewicz, M. et al. "Differential Ligand Binding Specificities of the Pulmonary Collectins Are Determined by the Conformational Freedom of a Surface Loop" Biochemistry, vol. 56 No. 31, 2017, pp. 4095-4105. (Abstract Only).

\* cited by examiner

SYSTEMS AND METHODS FOR CHARACTERIZING SURFACTANT PROTEIN D (SP-D) OLIGOMERS

CROSS-REFERENCE TO RELATED APPLICATIONS

This application is the U.S. National Phase of PCT/US2019/024320 filed Mar. 27, 2019 which published in English as WO 2019/191254 on Oct. 3, 2019 which claims priority to U.S. Prov. App. No. 62/650,138 filed Mar. 29, 2018 entitled "METHODS FOR CHARACTERIZING SURFACTANT PROTEIN D (SP-D) OLIGOMERS" which are each incorporated by reference herein in its entirety.

PARTIES TO A JOINT RESEARCH AGREEMENT

The presently claimed invention was made by or on behalf of the below listed parties to a joint research agreement. The joint research agreement was in effect on or before the date the claimed invention was made, and the claimed invention was made as a result of activities undertaken within the scope of the joint research agreement. The parties to the joint research agreement are Airway Therapeutics, LLC (currently d/b/a Airway Therapeutics, Inc.) and Glycotope GmbH.

REFERENCE TO SEQUENCE LISTING

The present application is being filed along with a Sequence Listing in electronic format. The Sequence Listing is provided as a file entitled AIRWY013NPSEQLIST, created Sep. 24, 2020, which is approximately 7 Kb in size. The information in the electronic format of the Sequence Listing is incorporated herein by reference in its entirety.

FIELD OF THE INVENTION

Some embodiments of the methods and compositions provided herein include identifying and/or quantifying oligomeric species of surfactant protein-D (SP-D). Some embodiments include performing an asymmetric flow field-flow fractionation with multi-angle laser light scattering (AF4-MALLS) analysis on the SP-D.

BACKGROUND OF THE INVENTION

Mammalian pulmonary surfactant is a mixture of proteins (10%) and lipids (90%) including the major lipid component dipalmitoylphosphatidylcholine (Zuo Y Y, et al., Biochim Biophys Acta (2008) 1778:1947-77). The main function of the pulmonary surfactant is to ensure minimal surface tension within the lung to avoid collapse during respiration. Furthermore, by interacting with inhaled pathogens, the pulmonary surfactant also participates in host defense (Clements J A. Am Rev Respir Dis (1977) 115:67-71). Pulmonary surfactant deficiency is, therefore, associated with pulmonary diseases such as asthma, bronchiolitis, respiratory distress syndrome (RDS), cystic fibrosis, and pneumonia (Griese $M_w$. Eur Respir J (1999) 13:1455-76). Surfactant formulations are indicated for the treatment of RDS, which affects ~1.5 million premature babies globally every year. Respiratory distress syndrome is a major pulmonary surfactant deficiency disease caused by the structural immaturity of the lungs in premature infants, which makes it difficult to breathe, inhibits gas exchange, and promotes alveolar collapse (Notter R H. 2000 Lung Surfactants. Basic Science and Clinical Applications. New York, NY: Marcel Dekker Inc.). However, treatment becomes more difficult if the lungs are infected or if there are inflammatory or oxidative complications, because current surfactant preparations lack surfactant protein D (SP-D). The successful treatment of complex pulmonary diseases, therefore, requires the production of surfactant formulations whose composition matches natural pulmonary surfactant as closely as possible (Robertson B, et al., Biochim Biophys Acta (1998) 1408:346-61).

SP-D has a role in the pulmonary innate immune system by providing anti-inflammatory and antimicrobial activities that address chronic pulmonary diseases such as asthma, cystic fibrosis, and smoking-induced emphysema (Clark H, et al., Immunobiology (2002) 205:619-31). Data based on premature newborn lambs suggest that the administration of ~2-3 mg/kg of recombinant human SP-D in combination with 100 mg/kg Survanta® (a natural surfactant available in USA) is more effective than Survanta® alone for the prevention of endotoxin shock and the reduction of lung inflammation caused by ventilation (Ikegami M, et al., Am J Respir Crit Care Med (2006) 173:1342-7; Sato A, et al., Am J Respir Crit Care Med (2010) 181:1098-105).

Traditionally, SP-D has been isolated from the supernatant of bronchoalveolar lavage or amniotic fluid, but most SP-D is lost during purification, in part due to the hydrophilic properties of SP-D (Dodagatta-Marri E, et al., Methods Mol Biol (2014) 100:273-90). The use of recombinant human surfactant protein D (rhSP-D) to supplement pulmonary surfactant formulations can ensure therapeutic efficacy because current pulmonary surfactant formulations lack the ability to effectively modulate the host immune response in the absence of the hydrophilic surfactant proteins. A characteristic of native SP-D that must be maintained in any pharmaceutical composition is the appropriate oligomerization state because the higher-order multimerization in the endogenous surfactant protein increases the number of SP-D-binding sites to carbohydrate ligands on the surface of pathogens, achieving potent bacterial and viral agglutination effects (White M, et al., J Immunol (2008) 181:7936-43). The appropriate oligomerization state is also required for receptor recognition and receptor-mediated signal transduction for modulation of the host immune response (Yamoze M et al., J Biol Chem (2008) 283:35878-35888) as well as for maintenance of surfactant homeostasis (Zhang L et al., J Biol Chem (2001) 276:19214-19219). The low SP-D yields and variable oligomerization states make it difficult to use natural sources for the production of pharmaceutical SP-D (Strong P, et al., J Immunol Methods (1998) 220:139-49). To overcome some of these limitations, recombinant SP-D can be produced in microbes or mammalian cell lines, potentially offering a large-scale platform for the production of homogeneous recombinant SP-D formulations. However, recombinant SP-D can have variable oligomerization states and/or inactive aggregate forms, therefore reducing the potential efficacy of such preparations. Therefore, there is a need for methods that can be used to discriminate active oligomeric forms from the inactive aggregate forms, and to quantitate the oligomeric forms to ensure reproducible quality from the manufacturing process.

SUMMARY OF THE INVENTION

Some embodiments of the methods and compositions provided herein include methods to determine the activity of a pharmaceutical composition comprising surfactant protein-D (SP-D). Some such embodiments include a method comprising: measuring the relative proportion of oligomeric species of SP-D in the pharmaceutical composition; and calculating the relative proportion of SP-D dodecamers in the pharmaceutical composition, thereby determining the activity of the pharmaceutical composition. Some embodiments also include calculating the relative proportion of SP-D aggregate having an average radius greater than 70 nm or root mean square (RMS) radius greater than 70 nm in the pharmaceutical composition. In some embodiments, the measuring comprises performing an asymmetric flow field-flow fractionation with multi-angle laser light scattering (AF4-MALLS) analysis. In some embodiments, calculating comprises providing a model of the oligomeric species of SP-D comprising rod-like geometries and spherical-like geometries. In some embodiments, the model comprises a Zimm model and a second order Debye model of the oligomeric species of SP-D. Some embodiments also include measuring the relative proportion of at least one SP-D oligomeric species in the SP-D sample, wherein the SP-D oligomeric species is selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm.

Some embodiments of the methods and compositions provided herein include to determine the relative proportion of oligomeric species of surfactant protein-D (SP-D) in a sample, comprising: performing an asymmetric flow field-flow fractionation with multi-angle laser light scattering (AF4-MALLS) analysis on the SP-D sample; and determining the relative proportion of an oligomeric species of SP-D from the results of the AF4-MALLS analysis, wherein the SP-D oligomeric species is selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm. Some embodiments also include measuring the relative proportion of SP-D dodecamers in the sample. Some embodiments also include measuring the relative proportion of SP-D aggregate having an average radius greater than 70 nm or RMS radius greater than 70 nm in the sample.

Some embodiments of the methods and compositions provided herein include a method to determine the relative proportion of active oligomeric species of surfactant protein-D (SP-D) in a sample, comprising: performing an asymmetric flow field-flow fractionation with multi-angle laser light scattering (AF4-MALLS) analysis on the SP-D sample; measuring the relative proportion of SP-D dodecamers in the SP-D sample; measuring the relative proportion of at least one SP-D oligomeric species in the SP-D sample selected from the group consisting of a SP-D trimer, a SP-D hexamer, a SP-D star-like oligomer having an average radius of 70 nm or RMS radius of 70 nm; and SP-D aggregate having an average radius greater than 70 nm or RMS radius greater than 70 nm; and calculating a ratio between each of the measured relative proportions. In some embodiments, the at least one SP-D oligomeric species comprises an SP-D aggregate having an average radius greater than 70 nm or RMS radius greater than 70 nm. Some embodiments also include integrating a fractogram from the AF4-MALLS analysis into peaks. Some embodiments also include measuring a relative peak area (RPA) of the fractogram for at least one peak indicative of a SP-D oligomeric species selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm. In some embodiments, the SP-D star-like oligomer has a molar mass less than or equal to about 6 MDa. In some embodiments, the SP-D aggregate has a molar mass greater than 6 MDa.

Some embodiments also include measuring the relative proportion of SP-D star-like oligomeric species in the sample having an average radius of 70 nm or RMS radius of 70 nm in the sample. Some embodiments also include measuring the relative proportion of SP-D aggregates having an average radius greater than 70 nm or RMS radius greater than 70 nm in the sample.

In some embodiments, the SP-D sample is predicted to have activity in a lipopolysaccharide-Toll-like receptor 4 (LPS-TLR4) assay, or in a bacterial aggregation assay. In some embodiments, the SP-D sample having a relative proportion of SP-D dodecamers greater than or equal to 35% of the SP-D oligomeric species in the sample is indicative of the SP-D sample having activity. In some embodiments, the SP-D sample having a relative proportion of SP-D aggregates having an average radius greater than 70 nm or RMS radius greater than 70 nm less than 5% of the total SP-D oligomeric species in the sample is indicative of the SP-D sample having activity.

In some embodiments, the AF4-MALLS is performed in the absence of a chelating agent selected from the group consisting of EDTA and EGTA.

In some embodiments, the SP-D is a recombinant human SP-D (rhSP-D). In some embodiments, the rhSP-D is derived from a human myeloid leukemia cell line expressing the rhSP-D from a transgene. In some embodiments, the rhSP-D comprises the amino acid sequence of SEQ ID NO:02. In some embodiments, the rhSP-D comprises a residue at a polymorphic position corresponding to a residue selected from the group consisting of Met11, Thr160, Ser 270, and Ala 286.

In some embodiments, the relative proportion the oligomeric species is with respect to mass. In some embodiments, the relative proportion the oligomeric species of SP-D is with respect to number of molecules. In some embodiments, the relative proportion the oligomeric species is with respect to a relative peak area (RPA) or an adjusted RPA in an AF4-MALLS analysis. In some embodiments, the SP-D dodecamer has a molecular weight of about 520 kDa.

Some embodiments of the methods and compositions provided herein include electronic systems for determining the activity of a pharmaceutical composition comprising surfactant protein-D (SP-D). Some such embodiments can include a system comprising a processor having instructions configured to execute the following steps: measuring the relative proportion of oligomeric species of SP-D in the pharmaceutical composition; calculating the relative proportion of SP-D dodecamers in the pharmaceutical composition; and determining the activity of the pharmaceutical composition based on the relative proportion of SP-D dodecamers, wherein a higher relative proportion of SP-D dodecamers is indicative of the composition having a higher level of activity compared to the activity of a composition having a lower relative proportion of SP-D dodecamers. In some embodiments, the activity comprises activity in a toll-like receptor 4 (TLR4) assay, or in a bacterial aggregation assay. Some embodiments also include calculating the relative proportion of SP-D aggregate having an average radius greater than 70 nm or RMS radius greater than 70 nm in the pharmaceutical composition. In some embodiments, the measuring comprises performing an asymmetric flow field-flow fractionation with multi-angle laser light scattering (AF4-MALLS) analysis. In some embodiments, the calculating comprises providing a model of the oligomeric species of SP-D comprising rod-like geometries and spherical-like geometries. In some embodiments, the model comprises a Zimm model and a second order Debye model of the oligomeric species of SP-D. Some embodiments also include measuring the relative proportion of at least one SP-D oligomeric species in the SP-D sample, wherein the SP-D oligomeric species is selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm.

Some embodiments of the methods and compositions provided herein include electronic systems for determining the relative proportion of oligomeric species of surfactant protein-D (SP-D) in a sample. Some such embodiments can include a system comprising a processor having instructions configured to execute the following steps: performing an asymmetric flow field-flow fractionation with multi-angle laser light scattering (AF4-MALLS) analysis on the SP-D sample; and determining the relative proportion of an oligomeric species of SP-D from the results of the AF4-MALLS analysis, wherein the SP-D oligomeric species is selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm. Some embodiments also include measuring the relative proportion of SP-D dodecamers in the sample. Some embodiments also include measuring the relative proportion of SP-D aggregate having an average radius greater than 70 nm or RMS radius greater than 70 nm in the sample.

Some embodiments of the methods and compositions provided herein include electronic systems for determining the relative proportion of active oligomeric species of surfactant protein-D (SP-D) in a sample. Some such embodiments include a system comprising a processor having instructions configured to execute the following steps: performing an asymmetric flow field-flow fractionation with multi-angle laser light scattering (AF4-MALLS) analysis on the SP-D sample; measuring the relative proportion of SP-D dodecamers in the SP-D sample; measuring the relative proportion of at least one SP-D oligomeric species in the SP-D sample selected from the group consisting of a SP-D trimer, a SP-D hexamer, a SP-D star-like oligomer having an average radius of 70 nm or RMS radius of 70 nm; and SP-D aggregate having an average radius greater than 70 nm or RMS radius greater than 70 nm; and calculating a ratio between each of the measured relative proportions. In some embodiments, the at least one SP-D oligomeric species comprises SP-D aggregate having an average radius greater than 70 nm or RMS radius greater than 70 nm. Some embodiments also include integrating a fractogram from the AF4-MALLS analysis into peaks. Some embodiments also include measuring a relative peak area (RPA) of the fractogram for at least one peak indicative of a SP-D oligomeric species selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm. In some embodiments, the SP-D star-like oligomer has a molar mass less than or equal to about 6 MDa. In some embodiments, the SP-D aggregate has a molar mass greater than 6 MDa. Some embodiments also include measuring the relative proportion of SP-D star-like oligomeric species in the sample having an average radius of 70 nm or RMS radius of 70 nm in the sample. Some embodiments also include measuring the relative proportion of SP-D aggregates having an average radius greater than 70 nm or RMS radius greater than 70 nm in the sample.

In some embodiments, the SP-D sample is predicted to have activity in a lipopolysaccharide-Toll-like receptor 4 (LPS-TLR4) assay, or in a bacterial aggregation assay.

In some embodiments, the SP-D sample having a relative proportion of SP-D dodecamers greater than or equal to 35% of the SP-D oligomeric species in the sample is indicative of the SP-D sample having activity.

In some embodiments, the SP-D sample having a relative proportion of SP-D aggregates having an average radius greater than 70 nm or RMS radius greater than 70 nm less than 5% of the total SP-D oligomeric species in the sample is indicative of the SP-D sample having activity.

In some embodiments, the AF4-MALLS is performed in the absence of a chelating agent selected from the group consisting of EDTA and EGTA.

In some embodiments, the SP-D is a recombinant human SP-D (rhSP-D). In some embodiments, the rhSP-D is derived from a human myeloid leukemia cell line expressing the rhSP-D from a transgene. In some embodiments, the rhSP-D comprises the amino acid sequence of SEQ ID NO:02. In some embodiments, the rhSP-D comprises a residue at a polymorphic position corresponding to a residue selected from the group consisting of Met11, Thr160, Ser 270, and Ala 286.

In some embodiments, the relative proportion the oligomeric species is with respect to mass. In some embodiments, the relative proportion the oligomeric species is with respect to a relative peak area (RPA) or an adjusted RPA in an AF4-MALLS analysis. In some embodiments, the SP-D dodecamer has a molecular weight of about 520 kDa.

DETAILED DESCRIPTION

Figure 1:
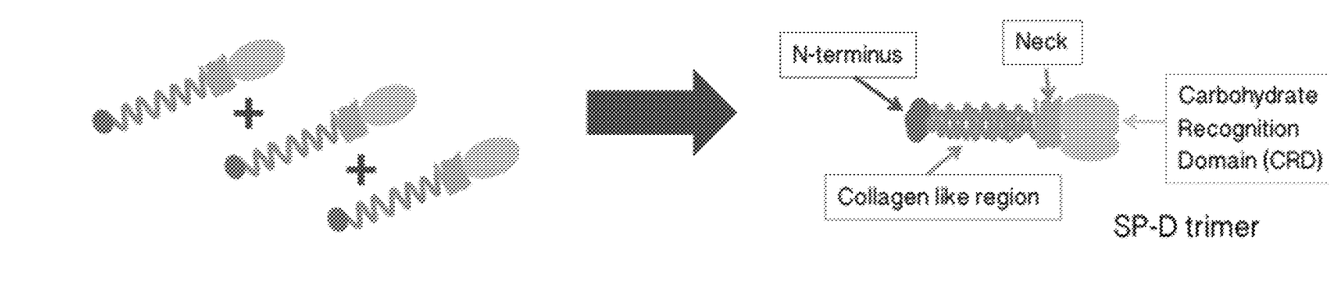
FIG. 1 is a schematic which depicts the formation of an SP-D trimer, and structural features of the SP-D trimer.

Surfactant protein D (SP-D) is a C-type ($Ca^{2+}$-dependent) lectin that comprises four domains: a cysteine-linked N-terminal region required for the formation of intermolecular disulfide bonds, a triple-helical collagen region, an α-helical-coiled-coil trimerizing neck peptide, and a C-terminal calcium-dependent carbohydrate-recognition domain (CRD) (Crouch E. et al. (1994) J Biol Chem, 269:17311-9). Monomers form trimers through folding of the collagenous region into triple helices and the assembly of a coiled-coil bundle of α-helices in the neck region (FIG. 1). These trimers are stabilized by two disulfide bonds in the cysteine-rich N-terminal domain. The SP-D trimer has a total molecular weight of 129 kDa which comprises three identical 43-kDa polypeptide chains. SP-D trimers can form higher oligomerization states which vary by size and conformation. Higher oligomerization states may be important for SP-D function (Hakansson K, et al., Protein Sci (2000) 9:1607-17; Crouch E. Respir Res (2000) 1:93-108; Crouch E. et al. (2006) J Biol Chem, 281:18008-14). The association of SP-D trimers into higher oligomerization states is sensitive to environmental factors and conditions during purification and storage. The pathway and type of interactions involved in the formation of large oligomers of SP-D have not been previously elucidated.

Some embodiments include a system and method of resolving oligomeric species of SP-D using a variation of the asymmetrical flow field-flow fractionation (AF4) technique. Some such embodiments were developed to resolve lower order SP-D species (hexamers and smaller) from the higher order SP-D species (dodecamer and larger). These embodiments allow the dodecamer form of SP-D to be clearly delineated within a complex fractogram envelope using multi-angle laser light scattering (MALLS). Using this variation of the AF4 technique, incorporating MALLS, allowed the molar mass of the dodecamer to be consistently determined at 521.8±3.6 kD over the analysis of numerous (n=102) samples. As used herein, the term "AF4-MALLS" means a method of performing asymmetrical flow field-flow fractionation followed by the use of multi-angle laser light scattering to identify the oligomeric species in the mixture being analyzed. The precision of the AF4-MALLS method was calculated to be ~5%. Fractograms of SP-D also displayed peaks associated with species larger than a dodecamer, which appeared as star-like species arising from dodecamer and/or hexamer assembly by atomic force microcopy (AFM) as well as aggregates that were larger than 70 nm in radius. Thus, embodiments that use the AF4-MALLS technique were found to provide a detailed profile of the various higher order oligomeric association states of SP-D, which were found to be determined with precision and accuracy.

Identification of Oligomeric Species of SP-D

A sample of SP-D can include several oligomeric species of the SP-D proteins, including: trimers, hexamers, dodecamers, and higher order oligomers such as star-like oligomeric species having an average root mean square (RMS) radius of about 70 nm, and aggregates which may have a radius greater than 70 nm. As described herein, certain oligomeric species of SP-D have been associated with certain useful activities. For example, SP-D dodecamers have been associated with antagonist activity in a Toll-like receptor 4 (TLR4) assay. A TLR4 assay can measure the activity of rhSP-D to inhibit lipopolysaccharide (LPS)-induced inflammatory cell responses by preventing LPS from binding/activating a TLR4 complex. Activity of the SP-D in an assay, such as a TLR4 assay can be a useful indicator for the predicted efficacy of the SP-D in certain methods of treatment. In addition, different samples of SP-D can contain different relative distributions of SP-D oligomeric species.

The distribution of oligomeric forms of recombinant human SP-D (rhSP-D) in a sample can be determined by a variety of techniques. Some embodiments can include identifying oligomeric species of rhSP-D by performing AFM. Some embodiments can include identifying oligomeric species of rhSP-D by performing a size exclusion chromatography such as high-performance liquid chromatography (HPLC). Some embodiments can include identifying oligomeric species of rhSP-D by performing polyacrylamide gel electrophoresis. In some such methods, a sample of rhSP-D can be contacted with an anionic detergent, such as of SDS, followed by contacting the sample with a crosslinking reagent, such as 1% glutardialdehyde. The crosslinked proteins can then be resolved by size using techniques such as polyacrylamide gel electrophoresis. Some methods can also include identifying the different oligomeric species of rhSP-D, such as performing a Western blot.

Some embodiments include performing an AF4-MALLS analysis on a SP-D sample. AF4 is a type of asymmetric field flow fractionation which is capable of rapid fractionation and high-resolution characterization of various particles including bio-molecules. See e.g., Giddings, J. C. et al., Science 193:1244-1245 (1976); Giddings, J. C. et al., Anal. Chem. 48:1126-1132 (1976); and Wagner et al., (2014) Anal Chem 86:5201-5210 which are each incorporated by reference in its entirety. AF4 can separate particles ranging from a few nanometers to a few micrometers. Field flow fractionation separation occurs in a thin flow channel which is comparable to a chromatographic separation column. An aqueous or organic solvent carries the sample through this channel. The flow through the channel is laminar due to the low channel height, and is the first force exerted on the sample. A second force is generated perpendicular to the channel flow. In AF4, one side of the flow channel is a membrane and the second force is fluid flow across the channel through the membrane. Particle separation occurs in this system because of these two forces. First, the velocity gradient due to the laminar flow within the channel causes particles in the center of the channel to move more quickly along the channel and be separated from those closer to the sides of the channel. Second, the second force forces the sample toward the membrane. Size separation occurs because the smaller molecules diffuse back toward the center of the channel more quickly than larger particles and hence are separated from the larger particles due to the quicker solvent flow toward the center of the channel. In some embodiments, the AF4-MALLS is performed in the absence of a chelating agent, such as EDTA and EGTA.

Some embodiments include determining the relative proportion of active oligomeric species in the SP-D sample, wherein the SP-D oligomeric species is selected from the group consisting of a SP-D trimer, a SP-D dodecamer, a SP-D star-like oligomer having an average radius of 70 nm or RMS radius of 70 nm, and a SP-D aggregate having an average radius or RMS radius greater than 70 nm. In some embodiments, the SP-D star-like oligomer can have a molar mass less than or equal to about 6 MDa. In some embodiments, the SP-D aggregate has a molar mass greater than 6 MDa.

Some embodiments also include integrating a fractogram from an AF4-MALLS analysis into peaks. A first peak in a fractogram (Peak 1) can include SP-D trimers and hexamers. A second peak in the fractogram (Peak 2) can include SP-D dodecamers. A third peak in the fractogram (Peak 3) can include intermediate species between SP-D dodecamers to SP-D star-like oligomers. A fourth peak in the fractogram (Peak 4) can include a heterogeneous mass of rhSP-D oligomers with constant RMS radius of about 70 nm consistent with what has been observed by AFM measurements for the star-like oligomeric species, and larger SP-D aggregate species having a radius greater than 70 nm.

Some embodiments also include determining, or measuring, a relative peak area (RPA) for a peak as a percentage of the total peak area of measured peaks, such as the four peaks identified above. Some such embodiments include measuring a relative peak area (RPA) of the fractogram for at least one peak indicative of a SP-D oligomeric species, such as a SP-D trimer, a SP-D dodecamer, a SP-D star-like oligomer having an average radius of 70 nm or RMS radius of 70 nm, and SP-D aggregate having an average radius greater than 70 nm or RMS radius greater than 70 nm.

In some embodiments, an SP-D sample having a relative proportion of SP-D dodecamers greater than or equal to a certain percentage of the SP-D oligomeric species in the sample is indicative of the SP-D sample having activity, the percentage can be 20%, 25%, 30%, 35%, 40%, 45%, 50%, 55%, 60%, 65%, 70%, 75%, 80%, 85%, 90%, 95%, and any percentage between any two of the foregoing percentages.

In some embodiments, an SP-D sample having a relative proportion of SP-D aggregates less than a certain percentage of the SP-D oligomeric species in the sample is indicative of the SP-D sample having activity, the percentage can be 40%, 35%, 30%, 25%, 20%, 15%, 10%, 5%, 3%, 2%, 1% and any percentage between any two of the foregoing percentages.

In some embodiments, the relative proportion the SP-D oligomeric species can be with regard to mass, number of molecules/aggregates in a population of SP-D different oligomeric species, or relative peak area (RPA) in an AF4-MALLS analysis.

In some embodiments, the SP-D comprises a wild-type human SP-D polypeptide. In some embodiments, the SP-D includes a polymorphism of the human SP-D polypeptide. Example SP-D polypeptide sequences are provided in TABLE 1. Polymorphisms in the human SP-D polypeptide can include: residue 11, ATG (Met)→ACG (Thr); residue 25, AGT (Ser)→AGC (Ser); residue 160, ACA (Thr)→GCA (Ala); residue 270, TCT (Ser)→ACT (Thr); and residue 286, GCT (Ala)→GCC (Ala) in which the positions relate to a position in a mature SP-D polypeptide, such as the example polypeptide of SEQ ID NO:02. In some embodiments, the rhSP-D comprises a certain residue at a polymorphic position in which the residue selected from Met11/31, Thr160/180, Ser 270/290, and Ala 286/306 in which residue positions relate to a position in the mature SP-D polypeptide, such as example SEQ ID NO:02, and a position in the SP-D polypeptide with its leader polypeptide, such as example SEQ ID NO:01. In some embodiments, the SP-D comprises Met11/31. In some embodiments, the rhSP-D comprises Met11/31, Thr160/180, Ser 270/290, and Ala 286/306. In some embodiments, the SP-D polypeptide has an identity with a polypeptide of SEQ ID NO:02 over the entire length of the polynucleotide of at least 80%, 90%, 95%, 99% and 100%, or any percentage in a range between any of the foregoing percentages.

sion vectors, rhSP-D polypeptides, cell-lines, and methods of purifying rhSP-D from such cells, are provided in U.S. 2019/0071693; and U.S. 2019/0071694 each of which is expressly incorporated by reference herein in its entirety.

Certain Systems

Some embodiments of the methods and compositions provided herein include electronic systems for determining the activity of a pharmaceutical composition comprising surfactant protein-D (SP-D). Some such embodiments can include a system comprising a processor having instructions configured to execute the following steps: measuring the relative proportion of oligomeric species of SP-D in the pharmaceutical composition; calculating the relative proportion of SP-D dodecamers in the pharmaceutical composition; and determining the activity of the pharmaceutical composition based on the relative proportion of SP-D dodecamers, wherein a higher relative proportion of SP-D dodecamers is indicative of the composition having a higher level of activity compared to the activity of a composition having a lower relative proportion of SP-D dodecamers. In some embodiments, the activity comprises antagonist activity in a toll-like receptor 4 (TLR4) assay. Some embodiments also include calculating the relative proportion of SP-D aggregate having an average radius greater than 70 nm or RMS radius greater than 70 nm in the pharmaceutical composition. In some embodiments, the measuring comprises performing an asymmetric flow field-flow fractionation with multi-angle laser light scattering (AF4-MALLS) analysis. In some embodiments, the calculating comprises providing a model of the oligomeric species of SP-D comprising rod-like geometries and spherical-like geometries. In some embodiments, the model comprises a Zimm model and a second order Debye model of the oligomeric species of SP-D. Some embodiments also include measuring the relative proportion of at least one SP-D oligomeric species in the SP-D sample, wherein the SP-D oligomeric species is selected from the group consisting of a SP-D trimer, a SP-D hexamer, a SP-D dodecamer, a SP-D star-like oligomer having an average radius of 70 nm or RMS radius of 70 nm,

TABLE 1

| SEQ ID NO. | Sequence |
| --- | --- |
| SEQ ID NO: 01<br>SP-D polypeptide<br>including a leader<br>sequence (underlined)<br>and polymorphisms<br>(underlined) at: Met<br>31, Thr 180, Ser 290,<br>Ala 306 | MLLFLLSALVLLTQPLEGYLEAEMKTYSHRTMPSACTLV<br>MCSSVESGLPGRDGRDGREGPRGEKGDPGLPGAAGQAGM<br>PGQAGPVGPKGDNGSVGEPGPKGDTGPSGPPGPPGVPGP<br>AGREGPLGKQGNIGPQGKPGPKGEAGPKGEVGAPGMQGS<br>AGARGLAGPKGERGVPGERGVPGNTGAAGSAGAMGPQGS<br>PGARGPPGLKGDKGIPGDKGAKGESGLPDVASLRQQVEA<br>LQGQVQHLQAAFSQYKKVELFPNGQSVGEKIFKTAGFVK<br>PFTEAQLLCTQAGGQLASPRSAAENAALQQLVVAKNEAA<br>FLSMTDSKTEGKFTYPTGESLVYSNWAPGEPNDDGGS<br>EDCVEIFTNGKWNDRACGEKRLVVCEF |
| SEQ ID NO: 02<br>SP-D polypeptide of<br>SEQ ID NO: 01, without<br>leader sequence, and<br>polymorphisms<br>(underlined) at: Met<br>11, Thr 160, Ser 270,<br>Ala 286. | AEMKTYSHRTMPSACTLVMCSSVESGLPGRDGRDGREGP<br>RGEKGDPGLPGAAGQAGMPGQAGPVGPKGDNGSVGEPGP<br>KGDTGPSGPPGPPGVPGPAGREGPLGKQGNIGPQGKPGP<br>KGEAGPKGEVGAPGMQGSAGARGLAGPKGERGVPGERGV<br>PGNTGAAGSAGAMGPQGSPGARGPPGLKGDKGIPGDKGA<br>KGESGLPDVASLRQQVEALQGQVQHLQAAFSQYKKVELF<br>PNGQSVGEKIFKTAGFVKPFTEAQLLCTQAGGQLASPRS<br>AAENAALQQLVVAKNEAAFLSMTDSKTEGKFTYPTGESL<br>VYSNWAPGEPNDDGGSEDCVEIFTNGKWNDRACGEKRLV<br>VCEF |

In some embodiments, the SP-D is a recombinant human SP-D (rhSP-D). In some embodiments, the rhSP-D is derived from a human myeloid leukemia cell line expressing the rhSP-D from an integrated transgene. Example expresand SP-D aggregate having an average radius greater than 70 nm or RMS radius greater than 70 nm.

Some embodiments of the methods and compositions provided herein include electronic systems for determining the relative proportion of oligomeric species of surfactant protein-D (SP-D) in a sample. Some such embodiments can include a system comprising a processor having instructions configured to execute the following steps: performing an asymmetric flow field-flow fractionation with multi-angle laser light scattering (AF4-MALLS) analysis on the SP-D sample; and determining the relative proportion of an oligomeric species of SP-D from the results of the AF4-MALLS analysis, wherein the SP-D oligomeric species is selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm. Some embodiments also include measuring the relative proportion of SP-D dodecamers in the sample. Some embodiments also include measuring the relative proportion of SP-D aggregate having an average radius greater than 70 nm or RMS radius greater than 70 nm in the sample.

Some embodiments of the methods and compositions provided herein include electronic systems for determining the relative proportion of active oligomeric species of surfactant protein-D (SP-D) in a sample. Some such embodiments include a system comprising a processor having instructions configured to execute the following steps: performing an asymmetric flow field-flow fractionation with multi-angle laser light scattering (AF4-MALLS) analysis on the SP-D sample; measuring the relative proportion of SP-D dodecamers in the SP-D sample; measuring the relative proportion of at least one SP-D oligomeric species in the SP-D sample selected from the group consisting of a SP-D trimer, a SP-D hexamer, a SP-D star-like oligomer having an average radius of 70 nm or RMS radius of 70 nm; and SP-D aggregate having an average radius greater than 70 nm or RMS radius greater than 70 nm; and calculating a ratio between each of the measured relative proportions. In some embodiments, the at least one SP-D oligomeric species comprises SP-D aggregate having an average radius greater than 70 nm or RMS radius greater than 70 nm. Some embodiments also include integrating a fractogram from the AF4-MALLS analysis into peaks. Some embodiments also include measuring a relative peak area (RPA) of the fractogram for at least one peak indicative of a SP-D oligomeric species selected from the group consisting of a SP-D trimer, a SP-D hexamer, a SP-D dodecamer, a SP-D star-like oligomer having an average radius of 70 nm or RMS radius of 70 nm, and SP-D aggregate having an average radius greater than 70 nm or RMS radius greater than 70 nm. In some embodiments, the SP-D star-like oligomer has a molar mass less than or equal to about 6 MDa. In some embodiments, the SP-D aggregate has a molar mass greater than 6 MDa. Some embodiments also include measuring the relative proportion of SP-D star-like oligomeric species in the sample having an average radius of 70 nm or RMS radius of 70 nm in the sample. Some embodiments also include measuring the relative proportion of SP-D aggregates having an average radius greater than 70 nm or RMS radius greater than 70 nm in the sample.

In some embodiments, the SP-D sample is predicted to have antagonist activity in a lipopolysaccharide-Toll-like receptor 4 (LPS-TLR4) assay.

In some embodiments, the SP-D sample having a relative proportion of SP-D dodecamers greater than or equal to 35% of the SP-D oligomeric species in the sample is indicative of the SP-D sample having activity. In some embodiments, an SP-D sample having a relative proportion of SP-D dodecamers greater than or equal to a certain percentage of the SP-D oligomeric species in the sample is indicative of the SP-D sample having activity, the percentage can be 20%, 25%, 30%, 35%, 40%, 45%, 50%, 55%, 60%, 65%, 70%, 75%, 80%, 85%, 90%, 95%, and any percentage between any two of the foregoing percentages.

In some embodiments, the SP-D sample having a relative proportion of SP-D aggregates having an average radius greater than 70 nm or RMS radius greater than 70 nm less than 5% of the total SP-D oligomeric species in the sample is indicative of the SP-D sample having activity. In some embodiments, an SP-D sample having a relative proportion of SP-D aggregates less than a certain percentage of the SP-D oligomeric species in the sample is indicative of the SP-D sample having activity, the percentage can be 40%, 35%, 30%, 25%, 20%, 15%, 10%, 5%, 3%, 2%, 1% and any percentage between any two of the foregoing percentages.

In some embodiments, the AF4-MALLS is performed in the absence of a chelating agent selected from the group consisting of EDTA and EGTA.

In some embodiments, the SP-D is a recombinant human SP-D (rhSP-D). In some embodiments, the rhSP-D is derived from a human myeloid leukemia cell line expressing the rhSP-D from a transgene. In some embodiments, the rhSP-D comprises the amino acid sequence of SEQ ID NO:02. In some embodiments, the rhSP-D comprises a residue at a polymorphic position corresponding to a residue selected from the group consisting of Met11, Thr160, Ser 270, and Ala 286.

In some embodiments, the relative proportion the oligomeric species is with respect to mass. In some embodiments, the relative proportion the oligomeric species is with respect to a relative peak area (RPA) or an adjusted RPA in an AF4-MALLS analysis.

EXAMPLES

Example 1—Atomic Force Microscope Analysis of rhSP-D

Oligomeric species of a recombinant human SP-D (rhSP-D) were characterized by atomic force microscope (AFM). See e.g., Arroyo R, et al. (2017) Biophysical Journal 112 (3): 503a, which is incorporated by reference in its entirety. A solution comprising 0.85 ng/µL rhSP-D in dilution buffer (200 mM NaCl, 20 mM Tris (pH 7.4), 1 mM EDTA) was placed on freshly cleaved mica substrate. Samples were imaged with an atomic force microscope from Nanotec (Nanotec Electriónica, Madrid, Spain) and PointProbePlus tips, type PPP-NCH (Nanosensors, Neuchâtel, Switzerland). The image size for quantitative studies was 1 µm×1 µm with 512 pixels, and was obtained at a rate of 1 line/second. Raw images were subjected to general plane subtraction, flattening with background subtraction, and artifact lines removal.

Oligomeric species identified in the obtained images included trimers, hexamers, dodecamers and star-like oligomers. Trimers had a rod-like appearance, and some trimers were measured to have an average length of about 65 nm (±8.6 nm). Dodecamers had an X-shaped appearance, and some dodecamers were measured to have a tip to opposite tip length of about 136 nm (±8.1 nm). The star-like species included members that had a star-shaped appearance composed of 6-20 trimers, each trimer joined to a particular member of this species through a central hub. Some star-like species were measured to have a diameter of about 140 nm, similar to the diameter of the measured dodecamers. TABLE 2 summarizes the distribution and frequency of observed oligomeric species.

TABLE 2

| Oligomeric species | No molecules | % molecules |
|---|---|---|
| Trimer | 244 | 37 |
| Hexamer | 100 | 15 |
| Dodecamer | 273 | 41 |
| Star-like | 45 | 7 |
| Total | 660 | 100 |

Example 2—AF4-MALLS Analysis of rhSP-D

The distribution of different oligomeric species of rhSP-D was determined by an AF4-MALLS analysis. For the AF4-MALLS analysis, rhSP-D samples were separated by an AF4 system (Eclipse Dual Tec, Wyatt Technology Corp., Santa Barbara, CA) followed by UV (Ultimate 3000 variable wavelength detector, Dionex Corporation, Sunnyvale, CA) and MALS analysis (Dawn Heleos II detector, Wyatt Technology Corp., Santa Barbara, CA). A Dionex Ultimate 3000 HPLC system (Dionex Corporation, Sunnyvale, CA) was used to inject the samples and deliver the mobile phase to the AF4 system. The AF4 configuration used a short channel with a 350 μm thick spacer (Wyatt Technology Corp., Santa Barbara, CA). Analysis of the data and calculations were performed using Chromeleon (Dionex Corporation, Sunnyvale, CA) and ASTRA (Wyatt Technology Corp., Santa Barbara, CA) software. Results from the AF4-MALLS analysis included a fractogram with several peaks.

The ASTRA software (version 6.1.1.17) calculated the following: molar mass and root means square (RMS) radius moments for each selected peak. Moments were referenced to averages over the entire sample, which can include many peaks. Equation (1) relates to the number-average molar mass:

$$M_n = \frac{\sum_i n_i M_i}{\sum_i n_i} = \frac{\sum_i c_i}{\sum_i c_i/M_i}.$$

An ASTRA measurement typically required an independent concentration determination. Since the relation between concentration (mg/mL) and number density (number/ml) was nM=c, the results from the equation (2) could be determined. Equation (2) relates to weight-average molar mass:

$$M_w = \frac{\sum_i n_i M_i^2}{\sum_i n_i M_i} = \frac{\sum_i c_i M_i}{\sum_i c_i}.$$

The polydispersity index value was: $\rho = M_w/M_n$. Typically, a value larger than 1.2 was considered polydisperse, while values less than 1.1 were designated as having low polydispersity.

In order to determine molar mass, mixed mathematical models were selected to calculate the size and MW of the molecule in an analysis of rhSP-D using light scattering data. As indicated herein, AFM images demonstrated that rhSP-D oligomeric species included monomers, dimers, trimers, hexamers, dodecamers, and higher order oligomeric structures. AFM images demonstrated structures that were rod-shaped, X-shaped and star-like. The star-like structures were measured by AFM and calculated to have a radius of about 70 nm, which were best characterized by a second order Debye model (P. Debye, "Molecular-weight determination by light scattering," J. Phys. Coll. Chem., vol. 51, pp. 18-32 (1947) which is incorporated by reference in its entirety). The Debye model uses the $R\theta/K^*c$ formalism and provided better results over a wider range of molar mass, including very large masses (greater than ~$10^6$ Daltons or ~100 nm RMS radius). The Debye model was applied to the analysis of peak 4 as described herein. The rod-shaped structures were measured by AFM and calculated to have a length of about 65 nm. The X-shaped structures were measured by AFM and calculated to a length of about 135 nm. Both the rod-shaped and X-shaped structures were best characterized by a rod-model. The Zimm equation was fitted to $R_\theta/K^*c$ vs $\sin(\theta/2)$. B. H. Zimm, J. Chem. Phys., vol. 16, pp. 1093-1099 (1948) which is incorporated by reference in its entirety. The theoretical form factor $P(\theta)$ for the desired model has been derived for spheres, coated spheres, and rods and are covered in the text by van de Hulst (H. C. van de Hulst, Light Scattering by Small Particles, Wiley, New York (1957), which is incorporated by reference in its entirety). The sphere and coated sphere models yielded geometric radii, while the rod model produced a length. The rod-model was applied to the analysis of peaks 1, 2 and 3 as described herein. The resultant rod-model is described by the equation below:

$$P(\theta) = \left(\frac{1}{u}\right) \int_0^{2u} \frac{\sin t}{t} dt - \frac{\sin^2 u}{u^2}$$

where $u = [(2\pi n_0/\lambda_0) L \sin(\theta/2)]$, and $L$ is the rod length, which is assumed to be much greater than its negligible diameter.

The diversity of SP-D structures could not be accommodated by a single model. Typically, the Zimm model can be sufficiently flexible to accommodate multiple geometries, but in the case of SP-D, a mixed modal analysis that combined the use of the second-order Debye model the rod model was used. The second order Debye model was applied to SP-D oligomeric species including aggregates having a radius greater than 70 nm (Peak 4). The rod model was applied to rod-like SP-D structures that included monomer, dimer, trimer, hexamer, and dodecamer (Peaks 1 and 2). There was a transition between dodecamer and the formation of star-like structures (Peak 3) for which the rod-model was applied for best characterization of MW. The mixed model better fit the AF4-MALLS data and was consistent with geometric measurements obtained by AFM.

Samples were integrated into four peak sections, Peaks 1-4, using a combination of analysis of the UV signal and an analysis of the molar mass as determined by light scattering. All relative areas were calculated using a drop-down integration at selected points. Peak 2 corresponded to a rhSP-D dodecamer peak, whose limits were determined by analyzing the molar mass and the polydispersity index. A center point, usually the highest point of the UV trace, and boundaries were set equidistant from that point. The polydispersity of that section is measured by Mw/Mn, as described herein. Typically, a value larger than 1.2 was considered polydisperse, while values less than 1.1 were designated as having low polydispersity. Boundaries were moved until the polydispersity index was about 1.05. Indices varied between 1.008 and 1.090. It was observed that slight movements of the peak boundaries could cause changes in the index. Peak 3 boundaries were set from the later boundary of Peak 2 until the dip in the UV trace found at 36.5 minutes. The outer boundary of peak 4 was set at 45 minutes. At 45 minutes the cross-flow had been turned off. Any material remaining in the channel began to elute at that time and there was effectively no separation taking place. Peak 1 included all species lower than a rhSP-D dodecamer. In some cases, lower molecular weight species were resolved, and separate integrations were performed. It was possible to superimpose the MW trace over the UV trace and integration points were found for hexamers (258 kDa), trimers (129 kDa), dimers (86 kDa) and monomers (42 kDa). The peaks were quite narrow and could be reliably determined.

In an initial series of studies, the cross-flow parameters were investigated using the original mobile phase composition (20 mM Tris buffer, pH 7.4, 200 mM NaCl, 1 mM EDTA). Once the cross-flow program was established, a series of experiments investigated the effects of the mobile phase composition, resulting in the removal of EDTA from the mobile phase comprised of 20 mM Tris, 200 mM NaCl, pH 7.4. Final adjustments were made to the focus steps, resulting in a final method that has a run time of 59.2 minutes. TABLE 3 lists parameters used for the AF4.

TABLE 3

| Step | Start time (min) | End time (min) | Duration (min) | Mode | X flow start (ml/min) | X flow end (ml/min) |
|---|---|---|---|---|---|---|
| 1 | 0 | 1 | 1 | Elution | | |
| 2 | 1 | 2 | 1 | Focus | | |
| 3 | 2 | 3 | 1 | Focus + inject | | |
| 4 | 3 | 6 | 3 | Focus | | |
| 5 | 6 | 6.2 | 0.2 | Elution | 0.5 | 3 |
| 6 | 6.2 | 9.2 | 3 | Elution | 3 | 3 |
| 7 | 9.2 | 19.2 | 10 | Elution | 3 | 0.18 |
| 8 | 19.2 | 29.2 | 10 | Elution | 0.18 | 0.18 |
| 9 | 29.2 | 44.2 | 15 | Elution | 0.18 | 0 |
| 10 | 44.2 | 54.2 | 10 | Elution | 0 | 0 |
| 11 | 54.2 | 59.2 | 5 | Elution + Inject | 0 | 0 |

Detector Flow: 0.5 ml/min
Inject Flow: 0.2 ml/min
Focus Flow: 0.5 ml/min
Injection Amount: 5 μg
UV detection: 214 nm
Mobile phase: 20 mM Tris, 200 mM NaCl, pH 7.4
Channel: short (145 mm)
Spacer: 350 μM
Membrane: 10 kD PES In another series of studies, 102 lyophilized formulations of rhSP-D obtained from 17 different cell-lines expressing the rhSP-D from an integrated transgene were analyzed. These includes cell-lines: S888, S990, S991, S1010, S2099, and twelve cell-lines numbered 2428 through 2439. The reproducibility of the AF4 method was gauged using four different metrics: (i) total area under the fractogram, indicating precision, (ii) relative area of the dodecamer, (iii) calculated molar mass of the dodecamer from the MALLS data, and (iv) the polydispersity of the molar mass within the dodecamer peak envelope. The relative standard deviation (rsd) was calculated for each metric across all samples. On average, the total area under the fractogram, indicative of precision, displayed rsd values that ranged from 4.3% to 5.3%. In other words, the total area for these complex fractograms was reproducible within about 5% from run to run for a given sample. However, the relative area of the rhSP-D dodecamer in these samples varied widely, from about 25% to 65%, and these relative amounts were reproducible, with the rsd values ranging from about 5% to 6.5%. The average rsd for the molar mass calculated from the MALLS data was very low at 0.86%. Finally, the polydispersity index (PDI) values calculated from the MALLS data exhibited average rsd values of about 1.5%.

Data using AF4-MALLS was analyzed to determine absolute molar mass and size of rhSP-D at a certain time during elution. The size to mass ratio was indicative of the shape of the rhSP-D. From the size to mass ratio, it was determined that in the early stages of an elution (0-34 minutes) the rhSP-D molecule had a linear or rod-shape. For rod model calculations, the software assumed that the thickness of a rod-shaped particle was insignificant (0.0 nm) compared to its length. Rod lengths were determined to be consistent with AFM measurements of 136±8.1 nm (N=50 individual molecules). The later stages of the elution (34-45 minutes) for rhSP-D indicated that a more compact structure was being observed. A second order Debye model was employed for analysis of these stages of the elution. The second order Debye model provided better results over a wider range of molar masses, including the very large (greater than ~$10^6$ Daltons or ~50 nm RMS radius). For dodecamers of rhSP-D, molecular weight was determined to be 520.09+/-4.61 kDa (N=72 determinations).

A first peak in the fractogram (Peak 1) contained rhSP-D trimers and hexamers based on mass calculations according to the rod model. A second peak in the fractogram (Peak 2) contained rhSP-D dodecamers. A third peak in the fractogram (Peak 3) contained intermediate species between rhSP-D dodecamers to rhSP-D star-like oligomers based on the intermediate molecular weight as determined by the rod model. A fourth peak in the fractogram (Peak 4) contained a heterogeneous mass of rhSP-D oligomers with constant RMS radius of about 70 nm consistent with what has been observed by AFM measurements for the star-like oligomeric species, and larger species having a radius greater than 70 nm. Beyond 36 minutes in the fractogram, the RMS radius increased further, indicative of further aggregate species. The relative peak area (RPA) for each peak was determined as a percentage of the total peak area of the four peaks.

To determine the distribution of oligomeric species in solution using an AF4-MALLS analysis with a greater resolution, the species of Peak 4 were analyzed further. The maximal molecular weight for star-like rhSP-D oligomer was assumed to be about 6 MDa based on images from the AFM analysis. The maximal molecular weight was used as a nominal cut-off for distinguishing star-like rhSP-D oligomers from larger aggregates. However, rhSP-D oligomeric species associated with Peak 3 were included in the aggregate determination when the 6 MDa was used as a cutoff in the analysis. This was inconsistent with the clear onset of elution of a new peak near 34 minutes. A size-based cutoff of 70 nm was used in the analysis. The 70 nm cutoff almost exactly coincided with the beginning of Peak 4, as seen either by the UV trace or by the overall LS trace. Therefore, using the 70 nm cutoff was a more accurate measure to distinguish the presence of rhSP-D oligomeric aggregate.

An adjusted RPA was determined for each of Peaks 3 and 4. Specifically, aspects of the RPA of Peak 4 that corresponded to star-like oligomeric species having a constant RMS radius of about 70 nm were determined, and these aspects were removed from the RPA of Peak 4 and added to the RPA of Peak 3 to provide an adjusted RPA for Peak 4 and Peak 3. Thus, the RPA of Peak 1, RPA of Peak 2, adjusted RPA of Peak 3, and adjusted RPA of Peak 4 corresponded to the relative distributions of rhSP-D oligomeric species in the AF4-MALLS analysis for (1) trimers and hexamers; (2) dodecamers; (3) star-like oligomeric species having an RMS radius of about 70 nm; and (4) aggregates having an RMS radius greater than 70 nm, respectively.

An AF4-MALLS analysis was performed on three rhSP-D samples obtained from different human myeloid leukemia cell lines expressing rhSP-D from an integrated transgene. TABLE 4 summarizes the results.

TABLE 4

| | AF4-MALLS Relative peak area (%) [Average molar mass] | | | | | |
|---|---|---|---|---|---|---|
| rhSP-D sample | Peak 1 | Peak 2 | Peak 3 | Adjusted Peak 3 | Peak 4 | Adjusted Peak 4 |
| 7H8 | 0.79 ± 0.05 [75.1 ± 56.9] | 34.12 ± 0.23 [523.6 ± 3.1] | 59.75 ± 0.55 [2164 ± 72] | 61.30 ± 0.74 | 5.34 ± 0.33 [47190 ± 960] | 3.79 ± 0.23 |
| 1C4 | 11.85 ± 0.33 [142.9 ± 14.9] | 30.75 ± 0.13 [520.2 ± 2.7] | 51.95 ± 0.46 [3048 ± 71] | 54.39 ± 0.56 | 5.45 ± 0.21 [31650 ± 3025] | 3.01 ± 0.13 |
| 8B11 | 7.29 ± 0.34 [76.4 ± 6.6] | 44.37 ± 0.60 [522.8 ± 4.6] | 45.61 ± 0.78 [2520 ± 33] | 47.29 ± 0.90 | 2.72 ± 0.16 [2313 ± 412] | 1.04 ± 0.04 |

Averages ± standard deviations of triplicate determinations

As shown in TABLE 4, the rhSP-D sample 8B11 had an RPA for Peak 2 of 44.37% which was indicative of this sample having the highest relative amount of dodecamer of the three tested samples. The rhSP-D sample 8B11 had an adjusted RPA for Peak 4 of 1.04% which was indicative of this sample having the lowest relative amount of aggregates having an RMS radius greater than 70 nm, of the three tested samples.

Example-3 Activity of rhSP-D in a TLR4 Assay

The Toll-like receptors (TLRs) have a role in both the innate immune system and the adaptive immune system, and SP-D has activity to modulate signaling through TLRs, such as Toll-like receptor 2 (TLR2) and Toll-like receptor 4 (TLR4). See e.g., Haagsman H P et al., (2008) Neonatology 93:288-294; Yamazoe M. et al., (2008) J. Biol Chem. 283:35878-35888; and Vieira F. et al., (2017) Ann Anat 211:184-201 which are each incorporated by reference in its entirety. TLR4 activity may also modulate the severity of conditions, such as bronchopulmonary dysplasia (BPD) (Malash A H et al., (2016) Gene 592:23-28 which is incorporated by reference in its entirety). Thus, the activity of rhSP-D to modulate TLR4 activity was measured as an indication of the effect of rhSP-D on a host immune response. The activity of reconstituted formulations containing rhSP-D was tested in an LPS-TLR4 assay. In an LPS-TLR4 assay, reconstituted rhSP-D can inhibit lipopolysaccharide (LPS)-induced inflammatory cell responses by preventing LPS from binding/activating the Toll-like receptor 4 (TLR4). See e.g., Yamazoe M. et al., (2008) J. Biol Chem. 283:35878-35888.

The activity of reconstituted rhSP-D in an LPS-TLR4 assay was tested in a method substantially similar to the following method. HEK-Bue™ hTLR4 cells (InvivoGen, San Diego, CA, U.S.A.) were plated at a density ~20000 cells/well in 384-well plates and incubated with various concentrations of SP-D for 2 hours at 37° C., 5% CO2. LPS (E. coli O26:B6, L5543 Sigma Aldrich) at an $EC_{80}$ concentration was added to each well, and the cells incubated for another 22 hours at 37° C., 5% $CO_2$. TLR4 activity was measured by detaching the cells from the wells, washing the suspended cells, resuspending the cells in PBS and removing any clumps by gentle pipetting. Washed cells were transferred to a 384-well plate at a density of $20e10^3$ cells/well containing HEK blue detection medium (Invivo-Gen, San Diego, CA, U.S.A.) that had been made up in endotoxin-free water containing 5 mM $CaCl_2$) and 1% (v/v) BSA. Cells were incubated at 37° C. in 5% $CO_2$ for 24 hours, and activity of TLR4 was determined by measuring the activity of a secreted embryonic alkaline phosphatase (SEAP) reporter gene using a spectrophotometer at 655 nm.

An $IC_{50}$ value for the SP-D was determined using nonlinear regression analysis by fitting the data to the four-parameter logistics equation. Because only the logarithm of the $IC_{50}$ values were normally distributed, for the purposes of averaging numbers from a series of experiments, the $pIC_{50}$ values were used, defined as the $-Log_{10}$ ($IC_{50}$). A curve span was determined from the difference between the fitted maximal response ($E_{max}$) and the fitted minimal response ($E_{min}$) and corresponds to the amplitude of the dose-response curve, or efficacy of the response. The results of an LPS-TLR4 assay with rhSP-D samples are summarized in TABLE 5.

TABLE 5

| rhSP-D Sample | Avg $pIC_{50}$ ± SD (mg/ml) | $IC_{50}$ (mg/ml) | Avg curve span ± SD | N |
|---|---|---|---|---|
| 7H8 | Not active | Not active | Not active | 5 |
| 1C4 | Not active | Not active | Not active | 3 |
| 8B11 | 3.00 ± 0.09 | 1.00E−03 | 37.64 ± 14.05 | 3 |
| 888 (+control) | 1.96 ± 0.14 | 1.10E−02 | 40.44 ± 13.64 | 4 |

As shown in TABLE 5, the rhSP-D sample 8B11 was the only tested cell clone sample that had activity in the TLR4 assay. Notably, the rhSP-D sample 8B11 was the only tested sample that had an RPA for Peak 2 greater than 35%.

Example 4—Activity of rhSP-D in a Bacterial Aggregation Assay

The activity of rhSP-D samples was tested in a bacterial aggregation assay. In a bacterial aggregation assay, active rhSP-D aggregates bacterial cells and reduces absorbance/increases transmission through the bacterial suspension. The bacterial aggregation assay was performed by a method substantially similar to the following method. Briefly, an exponential E. coli (ATCC: Y1088) culture was prepared, an aliquot was taken re-suspended in 1 mL buffer, (150 mM HEPES, 20 mM NaCl pH 7.4). Absorbance of the bacterial suspension was measured in a spectrometer at 700 nm, and the bacterial suspension was adjusted to obtain an Absorbance in the range of 1.0000 to 1.1000. 1M $CaCl_2$) was added to the suspension to obtain a final concentration of 5 mM $CaCl_2$). rhSP-D samples in placebo buffer (15 μl total volume for each dilution) were created at the following concentrations: 5, 1, 0.5, 0.25, 0.1, 0 μg/ml and added to cuvettes each containing 20 μL of the Hepes-NaCl buffer. 600 μL bacterial suspension were then added to cuvettes, and absorbance was measured every 2.5 minutes for each cuvette at 700 nm, for a total of 120 minutes. Tested concentrations of rhSP-D included 0 μg/ml, 0.1 μg/ml, 0.25 μg/ml, 0.5 μg/ml, 1.0 μg/ml, and 5.0 μg/ml. A percentage average aggregation at 60 minutes was calculated from the absorbance value at 60 minutes at each tested concentration, according to the following formula:

$$(1-abs) * 100 = \% \text{ Aggregation}$$

where 1=the measured absorbance of the *E. coli* suspension without rhSP-D.

Abs=The absorbance value of the *E. coli* suspension+rhSP-D at 60 minutes.

Percentage (%) Aggregation values were averaged from 3 replicates and imported, along with the standard deviation, into GraphPad Prism v7.0c, (GraphPad, La Jolla, CA 92037). The averaged values were fit using a 4-Parameter logistic curve. The resultant values for the EC50, and Span were determined for each reconstituted rhSP-D sample. pEC50 is the –Log 10 of the EC50.

The rhSP-D samples 7H8, 1C4 and 8B11 each had activity in the bacterial aggregation assay.

Example 5—Multivariate Analysis of rhSP-D Oligomeric Species

A multivariate statistical analysis was performed to determine any correlation between peaks observed in fractograms in AF4-MALLS analyses for various formulations of rhSP-D, and activity of rhSP-D samples in either the bacterial aggregation assay or the TLR4 assay. Digitized fractograms obtained from more than 40 different samples were used as a data matrix, and correlations to the measured $pIC_{50}$ values from the TLR4 assay, or $pEC_{50}$ results from bacterial aggregation activity assays were determined using PLS.

A full cross validation was performed on all calibration models using standard techniques. See e.g., Katz, M. H. "Multivariate Analysis: A Practice Guide for Clinicians." Cambridge University Press, New York, pp. 158-162 (1999); Stahle, L. et al., (1988) "Multivariate data analysis and experimental design in biomedical research. Prog. Med. Chem. 25: 291-338; Wold S. (2001) "PLS-regression: a basic tool of chemometrics." Chemom. Intell. Lab. Syst. 58: 109-130 which are each incorporated by reference in its entirety. Briefly, one sample was removed at a time, the data set was recalibrated, and a new model was constructed. This process was repeated until all the calibration samples were removed once and quantified as a validation model. Therefore, the first set, containing all samples was referred to as the calibration set and the one after cross-validation as the validation set. The jack-knife algorithm was used to determine statistical significance for any factor used in constructing partial least square (PLS) models (Martens, H. et al., (2001) "Multivariate Analysis of Quality: An Introduction" Wiley and Sons, Chichester, UK).

With regard to a correlation between particular peaks observed in the AF4-MALLS analysis and activity in the bacterial aggregation assay for various formulations of rhSP-D, the majority of the activity was found to reside in Peaks 1 and 2, with some persisting throughout Peak 3. A negative correlation was found between Peak 4 and activity in the bacterial aggregation assay. With regard to a correlation between particular peaks observed in the AF4-MALLS analysis and activity in the TLR4 assay for various formulations of rhSP-D, the activity was found to localize almost exclusively in the Peak 2. Thus, activity of rhSP-D in the TLR4 assay was directly related to dodecamer species of rhSP-D. Therefore, an AF4-MALLS provides a method to determine the proportion of the sample that includes dodecamers active in a TLR4 assay. Notably, the aggregate species with radius >70 nm found in corrected Peak 4 were not associated with activity in either the bacterial aggregation assay nor the TLR4 assay, confirming that these species represented inactive forms of rhSP-D.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it covers all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method to determine the activity of a pharmaceutical composition comprising surfactant protein-D (SP-D), the method comprising:

measuring the relative proportion of oligomeric species of SP-D in the pharmaceutical composition; and calculating the relative proportion of SP-D dodecamers in the pharmaceutical composition, thereby determining the activity of the pharmaceutical composition, wherein the activity comprises activity in a toll-like receptor 4 (TLR4) assay, the calculating comprises providing a model of the oligomeric species of the SP-D comprising rod-like geometries and spherical-like geometries, the model comprises a Zimm model and a second order Debye model of the oligomeric species of the SP-D, and the pharmaceutical composition having a relative proportion of SP-D dodecamers greater than or equal to 20% of the SP-D oligomeric species is indicative of the pharmaceutical composition having activity in the TLR4 assay.

2. The method of claim 1, wherein a composition having a higher relative proportion of SP-D dodecamers has a higher activity compared to a composition having a lower relative proportion of SP-D dodecamers.

3. The method of claim 1, further comprising calculating the relative proportion of SP-D aggregate having an average radius greater than 70 nm or RMS radius greater than 70 nm in the pharmaceutical composition.

4. The method of claim 1, wherein the measuring comprises performing an asymmetric flow field-flow fractionation with multi-angle laser light scattering (AF4-MALLS) analysis.

5. The method of claim 1, further comprising measuring the relative proportion of at least one SP-D oligomeric species in the pharmaceutical composition, wherein the SP-D oligomeric species is selected from the group consisting of a SP-D trimer, a SP-D hexamer, a SPD star-like oligomer having an average radius of 70 nm or RMS radius of 70 nm, and SP-D aggregate having an average radius greater than 70 nm or RMS radius greater than 70 nm.

6. A method to determine the relative proportion of oligomeric species of surfactant protein-D (SP-D) in a sample, comprising:
    performing an asymmetric flow field-flow fractionation with multi-angle laser light scattering (AF4-MALLS) analysis on the SP-D sample;
    determining the relative proportion of an oligomeric species of SP-D from the results of the AF4-MALLS analysis, wherein the SP-D oligomeric species is selected from the group consisting of a SP-D trimer, a SP-D hexamer, a SP-D dodecamer, a SP-D starlike oligomer having an average radius of 70 nm or RMS radius of 70 nm, and SP-D aggregate having an average radius greater than 70 nm or RMS radius greater than 70 nm, and differentiating the species using a Zimm model for rod-like geometries and a Debye model for spherical-like geometries, and
    measuring the relative proportion of SP-D dodecamers in the sample,
    wherein the sample having a relative proportion of SP-D dodecamers greater than or equal to 20% of the SP-D oligomeric species is indicative of the pharmaceutical composition having activity, and wherein the activity comprises activity in a toll-like receptor 4 (TLR4) assay.

7. The method of claim 6, further comprising integrating a fractogram from the AF4-MALLS analysis into peaks.

8. The method of claim 6, wherein the SP-D star-like oligomer has a molar mass less than or equal to 6 MDa.

9. The method of claim 6, wherein the AF4-MALLS is performed in the absence of a chelating agent selected from the group consisting of EDTA and EGTA.

10. The method of claim 6, wherein the relative proportion of the oligomeric species is with respect to mass.

11. The method of claim 6, wherein the relative proportion of the oligomeric species is with respect to a relative peak area (RPA) or an adjusted RPA in an AF4-MALLS analysis.

* * * * *

SEQUENCE LISTING

```
<160> NUMBER OF SEQ ID NOS: 2

<210> SEQ ID NO 1
<211> LENGTH: 375
<212> TYPE: PRT
<213> ORGANISM: Homo sapiens

<400> SEQUENCE: 1

Met Leu Leu Phe Leu Leu Ser Ala Leu Val Leu Leu Thr Gln Pro Leu
1               5                   10                  15
```

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Pro Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Thr Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

Ile Pro Gly Asp Lys Gly Ala Lys Gly Glu Ser Gly Leu Pro Asp Val
    210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                245                 250                 255

Gly Gln Ser Val Gly Glu Lys Ile Phe Lys Thr Ala Gly Phe Val Lys
            260                 265                 270

Pro Phe Thr Glu Ala Gln Leu Leu Cys Thr Gln Ala Gly Gly Gln Leu
        275                 280                 285

Ala Ser Pro Arg Ser Ala Ala Glu Asn Ala Ala Leu Gln Gln Leu Val
290                 295                 300

Val Ala Lys Asn Glu Ala Ala Phe Leu Ser Met Thr Asp Ser Lys Thr
305                 310                 315                 320

Glu Gly Lys Phe Thr Tyr Pro Thr Gly Glu Ser Leu Val Tyr Ser Asn
                325                 330                 335

Trp Ala Pro Gly Glu Pro Asn Asp Asp Gly Gly Ser Glu Asp Cys Val
            340                 345                 350

Glu Ile Phe Thr Asn Gly Lys Trp Asn Asp Arg Ala Cys Gly Glu Lys
        355                 360                 365

Arg Leu Val Val Cys Glu Phe
    370                 375

<210> SEQ ID NO 2
<211> LENGTH: 355
<212> TYPE: PRT
<213> ORGANISM: Homo sapiens

<400> SEQUENCE: 2

Ala Glu Met Lys Thr Tyr Ser His Arg Thr Met Pro Ser Ala Cys Thr
1               5                   10                  15

```
Leu Val Met Cys Ser Ser Val Glu Ser Gly Leu Pro Gly Arg Asp Gly
            20              25              30

Arg Asp Gly Arg Glu Gly Pro Arg Gly Glu Lys Gly Asp Pro Gly Leu
        35              40              45

Pro Gly Ala Ala Gly Gln Ala Gly Met Pro Gly Gln Ala Gly Pro Val
    50              55              60

Gly Pro Lys Gly Asp Asn Gly Ser Val Gly Glu Pro Gly Pro Lys Gly
65              70              75              80

Asp Thr Gly Pro Ser Gly Pro Pro Gly Pro Gly Val Pro Gly Pro
            85              90              95

Ala Gly Arg Glu Gly Pro Leu Gly Lys Gln Gly Asn Ile Gly Pro Gln
            100             105             110

Gly Lys Pro Gly Pro Lys Gly Glu Ala Gly Pro Lys Gly Glu Val Gly
        115             120             125

Ala Pro Gly Met Gln Gly Ser Ala Gly Ala Arg Gly Leu Ala Gly Pro
    130             135             140

Lys Gly Glu Arg Gly Val Pro Gly Glu Arg Gly Val Pro Gly Asn Thr
145             150             155             160

Gly Ala Ala Gly Ser Ala Gly Ala Met Gly Pro Gln Gly Ser Pro Gly
            165             170             175

Ala Arg Gly Pro Pro Gly Leu Lys Gly Asp Lys Gly Ile Pro Gly Asp
            180             185             190

Lys Gly Ala Lys Gly Glu Ser Gly Leu Pro Asp Val Ala Ser Leu Arg
            195             200             205

Gln Gln Val Glu Ala Leu Gln Gly Gln Val Gln His Leu Gln Ala Ala
    210             215             220

Phe Ser Gln Tyr Lys Lys Val Glu Leu Phe Pro Asn Gly Gln Ser Val
225             230             235             240

Gly Glu Lys Ile Phe Lys Thr Ala Gly Phe Val Lys Pro Phe Thr Glu
            245             250             255

Ala Gln Leu Leu Cys Thr Gln Ala Gly Gly Gln Leu Ala Ser Pro Arg
            260             265             270

Ser Ala Ala Glu Asn Ala Ala Leu Gln Gln Leu Val Val Ala Lys Asn
        275             280             285

Glu Ala Ala Phe Leu Ser Met Thr Asp Ser Lys Thr Glu Gly Lys Phe
    290             295             300

Thr Tyr Pro Thr Gly Glu Ser Leu Val Tyr Ser Asn Trp Ala Pro Gly
305             310             315             320

Glu Pro Asn Asp Asp Gly Gly Ser Glu Asp Cys Val Glu Ile Phe Thr
            325             330             335

Asn Gly Lys Trp Asn Asp Arg Ala Cys Gly Glu Lys Arg Leu Val Val
            340             345             350

Cys Glu Phe
        355
```